US005677355A

United States Patent [19]

Shalaby et al.

[11] Patent Number: 5,677,355
[45] Date of Patent: Oct. 14, 1997

[54] CONTINUOUS OPEN-CELL POLYMERIC FOAMS CONTAINING LIVING CELLS

[75] Inventors: Shalaby W. Shalaby, Anderson; Susan L. Roweton, Clemson, both of S.C.

[73] Assignee: Smith & Nephew, Inc., Memphis, Tenn.

[21] Appl. No.: 475,218

[22] Filed: Jun. 7, 1995

Related U.S. Application Data

[62] Division of Ser. No. 106,064, Aug. 13, 1993, abandoned.

[51] Int. Cl.$^6$ .................... C08J 9/26; A61K 9/14
[52] U.S. Cl. .................... 521/61; 521/63; 521/84.1; 521/102; 521/149; 521/182; 521/189; 264/41; 264/49; 424/93.1; 424/486
[58] Field of Search .................... 521/61, 63, 84.1, 521/102, 149, 182, 189; 264/41, 49; 424/93.1, 486

[56] References Cited

U.S. PATENT DOCUMENTS

| | | | |
|---|---|---|---|
| 4,603,076 | 7/1986 | Bowditch et al. | 428/246 |
| 4,828,772 | 5/1989 | Lopatin . | |
| 4,902,456 | 2/1990 | Yen et al. | 264/41 |
| 4,906,377 | 3/1990 | Yen et al. | 210/500.42 |
| 5,071,704 | 12/1991 | Fischel-Ghodsian | 428/354 |
| 5,098,621 | 3/1992 | Hermann | 264/46.4 |
| 5,130,342 | 7/1992 | McAllister et al. | 521/61 |

OTHER PUBLICATIONS

Aubert, J.H. and Sylwester, A.P., "Microcellular Foams? For What?," *Chemtech*, 1991, 21, pp. 234–238 (1991), American Chemical Society.

Aubert, J.H. and Sylwester, A.P., "Microcellular Foams? Here's How!," *Chemtech*, 1991, 21, pp. 290–295 (1991), American Chemical Society.

Aubert, J.H. and Clough, R.L., "Low–density, microcellular polystyrene foams," Sandia National Laboratories (Feb. 5, 1985).

Aubert, J., Sylwester, A., and Rand, P., "Microcellular Polymer Foams for Controlled Release and as Biomaterials," Sandia National Laboratories, pp. 447–448 (1991).

Renschler, C.L. and Sylwester, A.P., "Novel Forms of Carbon from Poly(acrylonitrile): Films and Foams," *Materials Science Forum*, vol. 52 & 53 (1989), pp. 301–322.

Roweton, S., "High Melting Solid Media for Production of Microporous Polymeric Foams," Patent Application Disclosure, Revised Aug. 4, 1993.

Roweton, S., "A New Approach to the Formation of Tailored Microcellular Foams and Microtextured Surfaces of Absorbable and Non–Absorbable Thermoplastic Biomaterials," Master of Science Thesis presented to Graduate School of Clemson University (Dec. 1993).

*Primary Examiner*—John M. Cooney, Jr.
*Attorney, Agent, or Firm*—Pravel, Hewitt, Kimball & Krieger

[57] ABSTRACT

A polymeric foam with continuous, open-cell pores containing living cells suitable for medical applications and methods for preparing these foams. The microporous foams are of controlled pore size that may be utilized in a variety of applications. In general, the foams are characterized in that the pores are continuous and open-celled. In preparing the foams, an organic polymer is melted and combined with a selected solid crystalline fugitive compound, that melts above about 25° C. and/or that sublimates at above about 25° C. or can be extracted, to produce a substantially isotropic solution. The solution is cooled under controlled conditions to produce a foam precursor containing the solidified fugitive composition dispersed through a matrix of the organic polymer. Crystals of fugitive composition are then removed by solvent extraction and/or sublimation, or a like process to produce microcellular foams having a continuous, open-cell structure. After removing the fugitive composition, living cells capable of producing biologically active products are added to the pores to produce a foam containing living cells.

13 Claims, No Drawings

CONTINUOUS OPEN-CELL POLYMERIC FOAMS CONTAINING LIVING CELLS

This is a division of application Ser. No. 08/106,064 filed Aug. 13, 1993 which is now abandoned.

BACKGROUND OF THE INVENTION

1. Field of the Invention

The invention relates to microporous thermoplastic foams and microtextured films and methods for preparing these foams and films. More specifically, the invention provides a method for producing foams with controlled pore size, chemical reactivity and mechanical properties, as well as microtextured surfaces with modulated microroughness, lyophilicity, and chemical reactivity that may be utilized in a variety of applications, including drug delivery systems, constructs for bone and cartilage regeneration, constructs for organ generation, filters for protein fractionation, matrices for gas and fluid filtration, templates for three-dimensional cell cultures, bioreactor substrate material, constructs containing immobilized chemical and biological reagents for use in continuous chemical and biochemical processing, and the like.

2. Description of the Related Art

It is expected that there are many potential biomedical applications for microcellular foams although not necessarily disclosed in the prior art. Among the potential uses are, use as timed-release drug delivery systems, neural regeneration pathways, templates for skin generation/regeneration, vascular replacements, and artificial bone templates. Specific areas of immediate biomedical significance include use of absorbable microcellular foams for bone and cartilage regeneration applications as well as the use of microcellular foams for organ generation, components of bioreactor cartridges, such as those useful for the production of growth factors, microcellular filters for protein fractionation, microcellular matrices for gas and fluid filtration, and microcellular constructs containing immobilized chemical and biological reagents for use in continuous chemical and biochemical processing, some of these applications are discussed in the patent literature.

For instance, U.S. Pat. Nos. 4,902,456 and 4,906,377 discuss the manufacture of fluorocarbon porous films from poly(tetrafluoroethylene-co-perfluoroalkyl vinyl ether) (PFA) or poly(tetrafluoroethylene-co-hexafluoropropylene) (FEP). The porous films are permeable to both liquids and gases and can be used as filtration media. In producing the films, a mixture is formed that comprises between about 10 to about 35 wt. % FEP or PFA polymer with the remainder being a solvent (porogen) chlorotrifluorethylene oligomer which permits liquid—liquid phase separation upon cooling from elevated temperature and subsequently solidification of the polymer. The mixture is heated and extruded to form a film or hollow fibers which are then quenched to effect phase separation of the fluorocarbon polymer from the solvent. The extrudate is quenched by passing it over a chill roller which cools the extrudate to a temperature that causes microphase separation of polymer and solvent. The solvent is separated from the polymer by extraction and the resultant microporous polymeric membrane is dried under restraint in order to minimize or prevent membrane shrinkage and collapse.

U.S. Pat. No. 4,603,076 relates to hydrophilic flexible foams that are said to be particularly suited for use in external biomedical applications. The polyurethane films are produced by blowing a methylene diphenyl diisocyanate (MDI) prepolymer with a substantially non-aqueous blowing agent, such as pressurized air. The prepolymer is then polymerized with polyoxyethylene polyol having at least two hydroxyl equivalents per mole. The hydrophilic foam may be extruded, knife coated, or cast into sheets.

Likewise, U.S. Pat. No. 5,071,704 relates to specific foams into which a reservoir layer maybe incorporated for allowing controlled release of vapors or liquids of an active compound into the surrounding environment. This is accomplished by incorporating a diffusion rate-limiting membrane layer, into a laminate of the foam, which controls the rate at which the active compound diffuses to the surface of the laminate and vaporizes or dissolves into the environment.

U.S. Pat. No. 5,098,621 relates to flexible foam substrates for selectively releasing and dispensing active ingredients. The composite material includes an open foam substrate containing particles of micropackaged active ingredient liquids or solids, formed with frangible containment walls, for breaking and releasing active ingredients in response to a defined level of stress.

Whereas the above patents indicate methods for making foams, microcellular foams made from biomedically significant polymers are of particular interest. Further, production of polymeric microporous foams having continuous cellular structures has not been exploited to any great extent. Microcellular foams have been produced using various materials and processes, but these foams cannot be produced from biomedically useful polymers using the two traditional methods: low temperature freeze drying and salt leaching, or the more recent technique, thermally induced phase separation (TIPS). Salt leaching has several limitations including the factor that it is often difficult to form small micropores with salt and it requires a high salt loading to achieve interpore channeling to produce continuous microporous foams. Further, there is a limited availability of solvents for polymers intended for biomedical use. Freeze drying also has its limitations. Specifically, there is a limited availability of crystallizable solvents that can be sublimed at the low temperatures characteristic of the freeze drying process. Further, the freeze drying process is a batch process which imposes limitations in terms of the size and shape of the foam produced.

TIPS, in concert with low-temperature freeze-drying technology, has been used to produce microcellular foams made of dextran, cellulose, and polystyrene. Limitations associated with available materials and solvents have generally restricted the growth of TIPS foam formation technology. In the TIPS process, the pore formation is preceded by a liquid—liquid, liquid-solid, or solid-liquid phase phase separation that is difficult to control. Further, the TIPS process requires solidifying the solvent-polymer mixture with rapid cryogenic quenching. This type of quenching presents an obstacle to large scale manufacturing processes.

Production of microcellular foams with controlled chemical and mechanical properties and morphology would facilitate the use of biologically safe polymers for the production of microcellular foams for biomedical applications. The growing demand for polymeric microcellular forms in several areas of advanced technology represent an urgent need for developing a method for converting non-bioabsorbable and bioabsorbable polymers, which cannot be processed in a traditional manner, to microcellular foams.

There exists a need for a continuous, open-cell microcellular foam, and a process for producing such a foam, on a typical manufacturing scale, from organic polymers suitable for biomedical applications, without need for complex new equipment to make the foams. Further, the process should be readily applicable to a broad range of thermoplastic polymers which can be absorbable or non-absorbable. Representative non-absorbable polymers include, but are not limited to, polyamides, aromatic polyesters, and polyolefins, while the absorbable type of polymers can be based totally or partially on polymers such as polylactic acid, polyglycolic acid, polyalkylene oxalate, polydioxanone, and polyanhydride. Further, the process should allow some measure of control of the size of the open-cell pores or voids so that foams may be custom tailored for particular applications, such as timed-release drug delivery systems, constructs for regeneration of bone, cartilage, and a multiplicity of soft tissues (including skin and liver) constructs for organ generation, filters for protein fractionation, matrices for gas and fluid filtration, constructs for use in bioreactor cartridges used for continuous chemical and biochemical processing, and the like. The inner and outer microporous cell surfaces can be chemically activated to allow the creation of chemically active functionalities which can be used to bind biologically active agents ionically or covalently.

SUMMARY OF THE INVENTION

The invention provides microcellular foams produced by a process that allows controlled formation of continuous open-cell pores or voids using a broad range of polymeric thermoplastic precursors and following processing schemes that are adaptable to a number of large manufacturing schemes. The foams have a matrix of an organic polymer with continuous, open-cell pores dispersed throughout the matrix, and are produced by a process that requires the blending of molten polymer with a relatively low molecular weight fugitive compound that is a crystalline solid that melts at temperatures above about 25° C. and/or can be sublimed and extracted in a broad range of temperatures above about 25° C.

In producing the microporous foams, an organic polymer is co-melted with the solid, crystalline, fugitive organic compound to produce a substantially isotropic solution. The isotropic solution is solidified by quenching, either by conventional cryogenic techniques or by ambient cooling, using a water or air as a convection medium, to produce a foam precursor. In most cases, the foam precursor is a matrix of 25 the organic polymer with a fugitive compound dispersed as a microcrystalline solid therein and a few cases as an intermolecular moiety with no distinct crystalline lattice. The fugitive compound can be removed by several techniques, depending upon the specific composition. Typically, the crystals are removed by leaching with a solvent or sublimation through heating under vacuum. The resultant continuous, open-cell foams are microporous and suitable for a variety of applications, among which are medical applications.

The inventive microporous foams can be made in a variety of shapes, depending upon requirements. For example, microporous foam in the form of hollow fibers, catheters, films or sheets, can be produced by extrusion of the molten, substantially isotropic solution that contains the organic polymer and the fugitive composition. The extrudate, consisting of a foam precursor, may then be treated to remove the fugitive composition either by leaching with a solvent, and/or sublimation of the composition. Alternatively, the foam precursor may be in the core of a fiber extrudate so that upon removal of the fugitive compound, an extrudate, with a hollow core and solid sheath is obtained.

Different forms of filamentous foams having a high surface area to volume ratio, may be used to fabricate bioreactors for producing a range of biological products. For example, living cells maybe cultured on the extensive surface area provided by these hollow fibers or tubes and, since the foam is of an open-cell nature, nutrients may readily be supplied to the cells and products readily removed for further processing and use. The structure of the foam also allows the facile transport of waste products.

Further, the open-cell foams may be fabricated of a bioabsorbable polymer, so that these may be implanted into a living body with or without the incorporation of certain bioactive agents, such as growth factors, for tissue regeneration purposes. Thus, the implanted bioabsorbable foam may be shaped and fitted as a prosthetic implant or construct to repair skeletal or soft tissues so that as bone or specific soft tissue grows into the bioabsorbable foam implant, the implant gradually absorbs until the skeletal or soft tissue structure is repaired and the implant completely absorbed. Specifically for bone generation, the pores of the bioabsorbable construct may be doped with bone morphogenic protein, or cells producing such proteins and other desirable biologically active substances, to promote healing and bone growth. Likewise, constructs may be fabricated for use in repairing ligament or soft tissue of living bodies utilizing bioabsorbable polymeric matrices, with suitable pharmacologically active and/or biologically active materials or cells producing such active materials, in the pores of the construct.

The foams which can be processed in the precursor stage by extrusion, casting or other methods for production of shaped articles, due to the custom tailored nature of the pores, are also useful as devices for the timed delivery of drugs, for instance transdermally. Thus, given the diffusion kinetics of a certain medicament, a foam may be custom tailored with a particular pore size which can be doped with the medicament to release the medicament to the patient at a controlled, desired rate.

The foam-precursor technology that is the subject of this invention can be used on a limited basis to create a thin microporous layer on the outer-most boundaries or surfaces of polymeric articles by dipping such articles in the fugitive composition medium to co-dissolve with the polymer comprising the base of the polymeric articles. Depending upon the dipping time and temperature, the thickness of the foamy parts can be modulated. This thin microporous layer can be from one to a few pores in thickness and can provide a means for surface microtexturing. Surfaces with variable foam depths can be achieved on high melting and/or low solubility polymers, such as polyetheretherketone (PEEK) and ultra high molecular weight polyethylene (UHMWPE). Orthopedic implants with porous outermost components facilitates bone-ingrowth into the implant and hence enhances development of mechanical stability. The performance of implants with microporous or textured surfaces can be further improved by chemical activation of the inner and outer cell walls by a process such as phophonylation. An alternate method to creating the desired surface morphology is obtained using the isotropic solution as a dipping medium, instead of the fugitive composition.

DETAILED DESCRIPTION OF THE PREFERRED EMBODIMENTS

The invention provides microcellular foams having a continuous, open-cell structure and a process for preparing such foams. The invention process permits a degree of control over the range of pore sizes so that the foams may be custom-tailored for specific applications. The applications include, but are not limited to, timed-release drug delivery systems, constructs for bone, cartilage and soft tissue regeneration, organ generation, filters for protein fractionation, microcellular matrices for gas and fluid filtration, bioreactors containing immobilized chemical and biological reagents for use in continuous chemical and biochemical processing to produce useful products.

Conventional foams, produced by traditional methods of foam formation, have voids or pores ranging from 50 to 100 microns in diameter. By some definitions, microcellular foams are those containing cells less than 50 microns in diameter. However, in the specification and claims, materials referred to as microcellular foams are those foams containing voids or pores of varying geometries, that are suitable for biomedical applications. Such foams preferably contain pores or voids with dimensions of from about 1 to about 400 microns, most preferably from about 5 to about 200 microns.

Foams, according to the invention, may be made from suitable organic polymeric materials, including the bioabsorbable and non-bioabsorbable thermoplastic polymers. The non-bioabsorbable medically significant polymers include the polyamides, polyesters, and polyolefins. The bioabsorbable polymers include poly(dioxanone), polyglycolic acid, polylactic acid, polyalkylene oxalates, polyanhydrides and copolymers thereof.

Depending upon the polymer selected and the size and distribution of voids or pores within the foam, the foams may range in mechanical properties from flexible to semi-flexible to rigid. Thus, foams according to the invention may be tailored for specific uses by judicious selection of polymer, and void or pore size, depending upon the intended use of the foam construct.

In order to prepare the foams according to the invention, a "fugitive composition" is required. These fugitive compositions are solid crystalline compositions that have molecular weights of less than about 300 daltons and that are able to form a substantially isotropic solution when combined with the molten polymer that will form the substrate of the foam. Upon cooling of the substantially isotropic polymer-fugitive compound solution, the fugitive compound should separate from the polymer by crystallizing or forming inter-macromolecular entities. This is realized through crystallization-induced microphase separation (CIMS). These crystals or entities may then be subsequently removed from the solidified polymer to produce voids or pores in the spaces they previously occupied. The preferred fugitive compound are those solid, crystalline compositions that melt at temperatures above about 25° C.; and those crystalline solid compositions that sublime at temperatures above about 25° C. and that may also be extracted with solvents. Examples of suitable fugitive compounds include salicylic acid, naphthalene, phenanthrene, anthracene, and tetramethylene sulfone.

Since the foams (including thin, foamy upper-most layers or surfaces) of the invention are produced using a solid that crystallizes, the size of the voids or pores may be controlled by controlling the relative rates of crystal growth and nucleation. Thus, for example, all other things being equal, if it is desired to produce smaller pores, then conditions must be selected to favor nucleation over crystal growth. This will ensure the presence of a relatively larger number of relatively small crystals dispersed throughout the solidified polymer matrix (the foam precursor). The crystals may then be removed from the foam precursor, either by (1) sublimation under suitable heat and/or vacuum, or (2) extraction with a solvent under suitable heat, (3) or both; to produce a foam containing small pores. If, on the other hand, a foam with larger pores or voids is desired, then process conditions should be modified to favor crystallization over nucleation. Under these circumstances, fewer crystal nuclei will be produced and the fugitive composition will crystalize into relatively fewer large crystals in a foam precursor. Upon removing these crystals from the foam precursor, relatively larger voids or pores will be produced in the open-cell foam.

In the process for producing the foams of the invention, the selected polymer is typically heated to above its melting temperature, to form a polymeric melt. This melt is combined with the selected fugitive composition that melts at above 25° C. of that sublimates at above about 25° C. The combination of molten polymer and fugitive compound produces a substantially isotropic solution. This solution may be solidified to produce a foam precursor including a solid polymeric matrix with crystals of the fugitive material dispersed throughout the matrix. As explained above, the relative size of the crystals may be determined by judicious selection of processing conditions. It is important to note that the quenching of the substantially isotropic solution to produce the foam precursor is not necessarily conventional cryogenic quenching wherein the solution is chilled by liquid nitrogen or dry ice (frozen carbon dioxide). Instead, the quenching step may be carried out by convective cooling with air or cooling in a water bath. This flexibility of the process of the invention is particularly important in that it allows the extruding of the substantially isotropic solution without need for cryogenic cooling of the extrudate as it exits the extrusion dye. Similarly, the casting of the foam precursors can be simplified.

Once the foam precursor is produced, regardless of whether by conventional cryogenic quenching or by water or air cooling, the fugitive composition, now finely dispersed throughout the foam precursor, must be removed in order to form the continuous, open-cell pores characteristic of the foams of the invention. These fugitive composition crystals may be removed by leaching with a solvent for the crystals, that is not a solvent for the polymer matrix. Thus, an important consideration in selecting the solvent is that it should be soluble in a solvent that is not a solvent for the organic polymer from which the foam will be made. Alternatively, if the solid crystalline material is one that sublimates at a temperature above 25° C., then it is important to select a polymer that retains its physical integrity by having a melting point (Tm) and/or glass transition temperature (Tg) well above the prevailing sublimation temperature and does not degrade at around the sublimation temperature of the solid fugitive compound.

The proportion of organic polymer and fugitive composition that must be mixed to produce a foam will vary depending upon the percentage of voids and the size range of the voids desired within the foam. Thus, if a large percentage voids is required, then a relatively larger proportion of the fugitive compound is added to the organic polymer. Minimum pore dimensions can be achieved with fugitive compositions proportions that allow only formation of inter-macromolecular entities. Typically, however, in order to produce a foam for biomedical applications, foams must have a percent voids ranging from about 25 to about 90 percent, more typically 50 to 80 percent, by volume. To produce such foams, from about 5 to about 90 wt. % fugitive composition should be added to the polymer; preferably, from about 10 to about 75 wt. % fugitive composition, based upon the combined weights of the polymer and fugitive composition and on the assumption that the fugitive composition and polymer have approximately similar densities.

It is known that certain polymeric materials do not readily form a solution with common organic solvents to create a porous or "foam-like" surface on the polymeric substrates. These are referred to as "polymers not readily soluble in conventional solvents." Among these polymeric materials are polyether-etherketone (PEEK), certain aromatic liquid crystalline polymides, polyesters and the like. In order to create a microporous morphology in the outer-most layers as surface layers, or microtexture the surfaces of substrates, especially films, of polymeric materials, according to the invention the polymeric material is subjected to hot, molten fugitive composition for a period of time sufficient to co-dissolve the surface of the film (or any other shaped articles) to a desired extent. Thereafter, the substrate is cooled and the solid crystalline material is removed by sublimation and/or extraction with a solvent, as explained above. As a result, the surface of the substrate exhibits continuous microporosity or is microtextured with pores or voids.

The invention also provides polymeric substrates with thin, continuously porous or microtextured surfaces. The microtexturing process according to the invention produces surfaces that have a porous texture with pore sizes ranging from less than about 1.0 microns up to about 20 microns in diameter in the surface of organic polymeric films and other substrates. In a broader sense, implants with modified surfaces and immediate subsurface micromorphology can be prepared by one of two methods. In a first method, the implant is coated with a thin layer of the isotropic solution containing both the desired polymer co-dissolved with the fugitive composition. The coating is then quenched, by a suitable process, to produce a thin layer of foam precursor that adheres to the surface of the implant. The fugitive composition is then removed from the foam precursor layer by solvent extraction, sublimation, or combination of these processes. The result is an implant with a thin microporous foam coating that allows tissue ingrowth so that the implant is better anchored in the body. The pores of the foam layer may be filled with pharmacologically or biologically active materials to facilitate healing, reduce risk of infection, and promote tissue growth.

In the event that the implant is fabricated from a polymeric composition or a polymeric composite, then the implant may be microtextured by coating with a medium containing a fugitive composition. The coated implant is then subjected to conditions that will cause the polymeric surface of the implant to co-dissolve or co-melt with the fugitive composition. Thus, the outer surface of the composite or polymer implant is converted into a foam precursor. This foam precursor can then be treated by solvent extraction or sublimation or both to remove the fugitive composition to produce a microtextured or microporous surface. The invention also provides bi-component constructs that include a foam core with a solid polymeric skin or surface layer surrounding the core. Such bicomponent constructs may be readily produced by several methods including, for instance, subjecting foam filaments produced, as described above, to heat to cause the outer surface to melt and flow and thereby form an outer skin. Alternatively, filaments maybe extruded a lower melting point polymeric sheet to facilitate subsequent melting of the outer layer to form the polymeric skin.

When the foams of the invention are intended for implantation into a living patient, then they maybe supplied with suitable medicaments, including growth factors, pharmacologically active compounds, and biologically active compounds or living cells capable of producing such biologically active compounds. The medicaments include antibacterial agents, anti-inflammatory agents, and the like. The biologically active agents include for example, insulin, insulin-like growth factor (IGF), fibroblast growth factor (FGF), epidermal growth factor (EGF), platelet-derived growth factor (PDGF), and the like. As a general principal, the foams may be doped with any agent or living cell capable of producing that agent in order to enhance the effectiveness of the foam in its intended function in the body. In one embodiment, the foams may be doped with a slightly soluble pharmaceutical product that may be added with the fugitive composition. The resultant foam precursor produced may be subjected to steps for removing the fugitive composition that result in retaining the pharmaceutical product in the voids or pores of the foam. Thus for instance, if the pharmaceutical product has higher thermal stability than a fugitive composition that is able to sublimate, then removal of the fugitive composition by sublimation will permit the retention of the medicament in the pores of the foam.

The following examples illustrate certain embodiments of the invention and do not in any way limit the scope of the invention as described above and claimed hereafter.

EXAMPLES

Example 1

Nylon 6 Microporous Foam Using Salicylic Acid As the Fugitive Composition

Nylon 6 fibers were heated with solid salicylic acid to form a 10% (by weight) Nylon 6 solution. The solution was heated close to, but not exceeding 230° C., in an inert atmosphere to produce an isotropic solution. The processing vessel was then quenched in 25° C. water bath. The solid foam precursor obtained was then heated to 78° C. while vacuum was applied to remove the salicylic acid by sublimation.

Characterization by light microscopy revealed a porous, foam morphology. Continuous porosity was verified by monitoring the fast transport of an aqueous dye solution through the foam.

Example 2

Nylon 12 Microporous Foam Using Salicylic Acid as the Fugitive Composition

Solid Nylon 12 pellets were heated with solid salicylic acid to form a 30% (by weight) isotropic solution while using mechanical stirring. The solution was heated to about 190° C. in an inert atmosphere and the processing vessel was then quenched in liquid nitrogen. The solid foam precursor obtained was washed with chloroform to remove the salicylic acid.

Characterization of the Nylon 12 foam was accomplished using scanning electron microscopy (SEM) and revealed a pore size of 50 to 100 microns. Continuous porosity was verified using the dye-transport method described in Example 1.

Example 3

Nylon 12 Microporous Foam Using Naphthalene

Solid Nylon 12 pellets were heated with solid naphthalene to form a 30% (by weight) isotropic solution while using mechanical stirring. The solution was heated to about 190° C. in an inert atmosphere and the vessel was then quenched in liquid nitrogen. The solid foam precursor obtained was washed with methanol which was cooled in liquid nitrogen to remove the naphthalene.

Characterization of the Nylon 12 form was accomplished using SEM and revealed a pore size of 30 to 50 microns. The dye transport method was used to verify the foam continuous porosity.

Example 4

Polyethylene Microporous Foam Using Naphthalene

Solid, high-density polyethylene pellets were heated with solid naphthalene to form a 30% (by weight) isotropic solution while applying mechanical stirring. The solution was heated to about 150° C. in an inert atmosphere and the vessel was then quenched in liquid nitrogen. The solid foam precursor obtained was washed with chloroform to remove the naphthalene.

Characterization of the polyethylene foam was accomplished using SEM and BET surface area analysis. The polyethylene foam was found to have pores ranging from 5 to 50 microns in diameter and a surface area of 2.3 square meters/gram. Continuous microporosity was verified using the dye transport method.

Example 5

Polypropylene Microporous Foam Using Naphthalene

Solid isotactic polypropylene pellets were heated with solid naphthalene to form a 20% (by weight) isotactic solution while applying mechanical stirring. The solution was heated to about 170° C. in an inert atmosphere and the processing vessel was then quenched in liquid nitrogen. The solid foam precursor obtained was washed with chloroform to remove the naphthalene.

Characterization of the polyethylene foam was accomplished using SEM and revealed pores ranging from i to 50 microns in diameter. Continuous porosity was verified using the dye transport method.

Example 6

Polycaprolactone Microporous Foam Using Naphthalene

Solid polycaprolactone (PCL) pellets were heated with solid naphthalene to form 20%, (by weight) isotropic solutions while applying mechanical stirring. The solutions were heated close to, but not exceeding, 140° C. in an inert atmosphere and the processing vessel was then quenched in liquid nitrogen. The solid foam precursor obtained was washed with hexane to remove the naphthalene.

Characterization of the polycaprolactone foams were accomplished using SEM and revealed pore sizes of 5 to 50 microns. Continuous porosity was verified using the dye transport method. Upon repeating this process, using 10, 20, 30 and 40 weight percent PCL to form foam precursors by casting into a precooled metallic mold, foams were obtained having pure porosity of 50 to 200μ depending on composition.

Example 7

Nylon 6 Microporous Foam Using Tetramethylene Sulfone

Solid Nylon 6 pellets were heated with tetramethylene sulfone to form a 20% (by weight) isotropic solution while applying mechanical stirring. The solution was heated to about 250° C. in an inert atmosphere and the process vessel was then quenched in liquid nitrogen. The solid foam precursor obtained was washed with methanol to remove the tetramethylene sulfone. Continuous porosity was verified using the dye transfer method.

Characterization of the nylon 6 foam was accomplished using SEM and revealed a pore size of 2 to 5 microns.

Example 8

Absorbable Microporous Foam Using Naphthalene

The absorbable copolyester of this example was prepared by catalyzed polycondensation of 75/25 (molar ratio) of diemthyl terephthalate/diethyl oxalate and 1.2 molar excess of trimethylene glycol in the presence of about 0.05 percent (by mole) stannous octoate as a catalyst. The polymerization was conducted in two stages. The first, the prepolymerization stage, was conducted at a temperature of 150°–180° C. under nitrogen at ambient pressure for about 6 hours. The second stage, post polymerization, was conducted under reduced pressure (less than 1 mmHg) at 180°–210° C. for about 8 hours. The resulting polymer was cooled, ground, and dried before use. The polymer exhibited an inherent viscosity (in $CHCl_3$ at 30° C.) of about 1.0 and a Tm of about 127° C.

Solid synthetic absorbable polyester was heated with naphthalene to form a 20% (by weight) isotropic solution while applying mechanical stirring. The solution was heated to about 230° C. in an inert atmosphere and the processing vessel was then quenched in liquid nitrogen. The solid foam precursor obtained was washed with n-hexane to remove the naphthalene. The purified foam exhibited the same inherent viscosity as that of the starting polymer.

Characterization of this absorbable polyester foam was accomplished by SEM.

Example 9

Absorbable Microporous Copolycaprolactone Foam Using Naphthalene

A solid absorbable copolycaprolactone (90/10 Caprolactone/Glycolide copolymer) was heated with naphthalene to form a 20% (by weight) isotropic solution while applying mechanical stirring. The solution was heated up to 120° C. in an inert atmosphere and the processing vessel was then quenched in liquid nitrogen. The solid foam precursor obtained was washed with n-hexane to remove the naphthalene. The inherent viscosity (in $CHCl_3$ @30° C.) of the foam was the same as that of the starting polymer (about 1.0).)

Characterization of this absorbable foam was accomplished using SEM and indicated a pore size of 1–150 microns. The continuous porosity was verified using the dye transport method.

Example 10

Absorbable Microporous 95/5 Copolycaprolatone Foam Using Naphthalene

A solid synthetic absorbable polyester (95/5 Caprolactone/Glycolide copolymer) was heated with naphthalene to form a 20% (by weight) isotropic solution while applying mechanical stirring. The solution was heated up to 110° C. in an inert atmosphere and the processing vessel was then quenched in liquid nitrogen. The solid foam precursor obtained was washed with n-hexane to remove the naphthalene. The purified foam exhibited the same inherent viscosity (in $CHCl_3$ @30° C.) as the starting polymer (about 0.8).

Characterization of the absorbable polyester foam was accomplished using SEM and indicated a pore size of 1–200 μm. The continuous porosity was verified by the dye diffusion method.

Example 11

Texturing of PEEK (Poly(ether-ether ketone) Film Using Naphthalene

A PEEK 10 mil-thick film sample (STABAR k200 manufactured by I.C.I.) was heated with naphthalene in an inert atmosphere for 2.5 hours at a temperature between 225° and 250° C. The treated film was removed and allowed to air cool at room temperature. The solid naphthalene was removed from the "surface" foam precursor using n-hexane after soaking for about 3 days.

Characterization of the resultant film surface was accomplished using SEM. A porous surface was evident with pore size diameters as small as 1 micron. The depth of the microporous layer was about 2–10 μm.

Example 12

Texturing of PEEK Film Using Salicylic Acid

A 10 mil thick PEEK film (STABAR K200) was heated with salicylic acid in an inert atmosphere for approximately 2 hours at a temperature of approximately 240° C. After air cooling the isolated film at room temperature, the solid salicylic acid was removed from the "surface" foam precursor using methanol after soaking for about 3 days.

Characterization of the resultant film surface was accomplished using SEM. A porous surface was evident with pore size diameters at or below 1 micron. The depth of the microporous layer was about 5–10 μm.

Example 13

Texturing of a Solid PEEK Coupon

A solid PEEK coupon was placed in liquid anthracene and maintained in an inert atmosphere for 3 hours at a temperature of approximately 260° C. After isolating and air cooling the polymer at room temperature, the solid anthracene was removed from the foam precursor obtained with hexane.

Characterization of the resultant sample surface was accomplished using SEM. A porous surface was evident with pore size diameters ranging from 1 to 50 micron. The depth of the microporous layer was shown to be about 20–200 μm.

Example 14

Extrusion of Microporous Polycaprolactone (PCL) Foam Fibers

Solid PCL was heated with naphthalene to form a 40% (by weight) isotropic solution while applying mechanical stirring. The solution was heated up to 145° C. in an inert atmosphere and the processing vessel was then quenched in liquid nitrogen. The co-solidified PCL/naphthalene foam precursor was then melt extruded at about 100° C. using a capillary equipped with a 40 mil die. The resulting filaments of foam precursor were air cooled and then washed with n-hexane to remove the naphthalene and produce PCL foam fibers. The inherent viscosity of the purified filaments was the same as that of the starting polymer (about 2.2 in $CHCl_3$ @30° C.).

Characterization of the PCL foam fibers was accomplished using SEM to ascertain their microporosity. The pore size ranged from 1–5 μm.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. A foam comprising:
   an organic polymeric matrix with continuous, open-cell pores dispersed therein; and
   living cells producing at least one product, the living cells contained in the pores,
   the foams produced by a process comprising the steps of:
      combining an organic polymer with a fugitive composition that is a solid cristalline material that melts above 25° C.
      co-melting and co-dissolving the fugitive composition with the polymer to produce a substantially isotropic solution;
      solidifying the isotropic solution to produce a foam precursor containing crystals of the fugitive composition;
      removing the crystals of the fugitive composition from the foam precursor to produce a continuous, open-cell foam; and
      adding selected living cells to the foam for inhabiting the pores and producing at least one product.

2. The foam of claim 1, wherein the foam is of a predetermined shape suitable for implantation into a living skeleton for repairing a wound and the at least one product includes a bone morphogenic protein.

3. The foam of claim 1, wherein the foam is adapted for implantation into a living body and the cells produce at least one biologically active compound that promotes reconstruction of damaged body tissue.

4. The foam of claim 1, wherein the cells utilize a nutrient medium to produce the product.

5. The foam of claim 4, wherein the foam is in the form of hollow fibers.

6. The foam of claim 2, wherein the organic polymer is a bioabsorbable polymer.

7. The foam of claim 3, wherein the organic polymer is a bioabsorbable polymer.

8. The foam of claim 6, wherein the bioabsorbable polymer is selected from the group consisting of polylactic acid, polyglycolic acid, polyalkylene oxalates, poly-p-dioxane, polyanhydrides, polymorpholinediones, polycaprolactone, and copolymers thereof.

9. The foam of claim 7, wherein the bioabsorbable polymer is selected from the group consisting of polylactic acid, polyglycolic acid, polyalkylene oxalates, poly-p-dioxane, polyanhydrides, polymorpholinediones, polycaprolactone, and copolymers thereof.

10. The foam of claim 2, wherein the foam is shaped as a prosthetic implant.

11. The foam of claim 3, wherein the foam is shaped as a prosthetic implant.

12. The foam of claim 1, wherein the pore diameter is in the range of about 1 micron to about 400 microns.

13. The foam of claim 1, wherein the living cells are adhered to walls of the pores.

* * * * *

UNITED STATES PATENT AND TRADEMARK OFFICE
CERTIFICATE OF CORRECTION

PATENT NO.    : 5,677,355
DATED         : October 14, 1997
INVENTOR(S)   : Shalaby W. Shalaby, et al.

It is certified that error appears in the above-identified patent and that said Letters Patent is hereby corrected as shown below:

On the title page, item [64] Assignee should read—Smith & Nephew Richards, Inc. Memphis, Tenn. --.

Signed and Sealed this

Second Day of June, 1998

*Attest:*

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO.   :   5,677,355
DATED        :   October 14, 1997
INVENTOR(S)  :   Shalaby W. Shalaby and Susan L. Roweton It is certified that error appears in the above-identified patent and that said Letters Patent is hereby corrected as shown below:

On title page, delete item [73]
  Assignee:  Smith & Nephew, Inc., Memphis, Tenn.

Signed and Sealed this

Twenty-third Day of June, 1998

Attest:

BRUCE LEHMAN

Attesting Officer

Commissioner of Patents and Trademarks